United States Patent [19]

King

[11] Patent Number: 5,191,104
[45] Date of Patent: Mar. 2, 1993

[54] ALKOXYLATION OF CARBOXYLATED COMPOUNDS

[75] Inventor: Stephen W. King, Scott Depot, W. Va.

[73] Assignee: Union Carbide Chemicals & Plastics Technology Corporation, Danbury, Conn.

[21] Appl. No.: 585,459

[22] Filed: Sep. 20, 1990

[51] Int. Cl.$^5$ ............................................. C07C 69/96
[52] U.S. Cl. ................................. 558/260; 560/29; 560/55; 560/115; 560/126; 560/160; 560/179; 562/465; 562/528; 562/588
[58] Field of Search ............ 560/179, 126, 55, 29, 560/115, 160; 562/465, 588, 508

[56] References Cited

U.S. PATENT DOCUMENTS

| | | | |
|---|---|---|---|
| 2,934,505 | 4/1960 | Gurgiolo | 260/2 |
| 3,328,306 | 6/1967 | Ellis | 252/90 |
| 3,432,445 | 3/1969 | Oagan et al. | 260/2 |
| 3,607,785 | 9/1971 | Oagan et al. | 252/431 C |
| 3,682,849 | 8/1972 | Smith et al. | 260/615 B |
| 4,022,808 | 5/1977 | Yoshihara et al. | 560/200 |
| 4,098,818 | 7/1978 | Krummel et al. | 260/535 R |
| 4,112,231 | 9/1978 | Weibull et al. | 544/174 |
| 4,115,415 | 9/1978 | Yoshihara | 560/200 |
| 4,210,764 | 7/1980 | Yang et al. | 568/618 |
| 4,223,164 | 9/1980 | Yang et al. | 568/618 |
| 4,239,917 | 12/1980 | Yang | 568/618 |
| 4,254,287 | 3/1981 | Ziegenhain et al. | 568/618 |
| 4,281,087 | 7/1981 | Heuschen et al. | 525/361 |
| 4,282,387 | 8/1981 | Olstowski et al. | 568/618 |
| 4,302,613 | 11/1981 | Yang et al. | 568/618 |
| 4,306,093 | 12/1981 | Yang et al. | 568/618 |
| 4,326,047 | 4/1982 | Yates | 525/507 |
| 4,359,589 | 11/1982 | Brownscombe | 568/618 |
| 4,360,698 | 11/1982 | Sedan | 568/618 |
| 4,375,564 | 3/1983 | Edwards | 568/618 |
| 4,396,779 | 8/1983 | Edwards | 568/618 |
| 4,396,780 | 8/1983 | Shtykh et al. | 568/620 |
| 4,453,022 | 6/1984 | McCain et al. | 568/618 |
| 4,453,023 | 6/1984 | McCain et al. | 568/618 |
| 4,465,877 | 8/1984 | Edwards | 568/618 |
| 4,472,560 | 9/1984 | Kuyper et al. | 526/120 |
| 4,474,678 | 10/1984 | Lutz et al. | 252/174.21 |
| 4,477,589 | 10/1984 | van der Hulst et al. | 502/169 |
| 4,490,561 | 12/1984 | Yang et al. | 568/615 |
| 4,568,774 | 2/1986 | Yang | 568/616 |
| 4,654,417 | 3/1987 | Inoue et al. | 528/416 |
| 4,659,778 | 4/1987 | Williams | 525/107 |
| 4,665,236 | 5/1987 | Edwards | 568/618 |
| 4,721,816 | 1/1988 | Edwards | 568/618 |
| 4,721,817 | 1/1988 | Edwards | 518/618 |
| 4,727,199 | 2/1988 | King | 568/620 |
| 4,754,075 | 6/1988 | Knopf et al. | 568/618 |
| 4,775,653 | 10/1988 | Leach et al. | 502/170 |
| 4,820,673 | 4/1989 | Knopf et al. | 502/167 |
| 4,886,917 | 12/1989 | Knopf et al. | 568/623 |
| 4,892,977 | 1/1990 | Nieh | 568/618 |
| 4,902,658 | 2/1990 | King et al. | 502/159 |

FOREIGN PATENT DOCUMENTS

| | | |
|---|---|---|
| 0026544 | 4/1981 | European Pat. Off. . |
| 0026546 | 4/1981 | European Pat. Off. . |
| 0026547 | 4/1981 | European Pat. Off. . |
| 0033359 | 6/1981 | European Pat. Off. . |
| 0082569 | 6/1983 | European Pat. Off. . |
| 0085167 | 6/1983 | European Pat. Off. . |
| 0095562 | 12/1983 | European Pat. Off. . |
| 0104309 | 4/1984 | European Pat. Off. . |
| 0180266 | 5/1986 | European Pat. Off. . |
| 0180267 | 5/1986 | European Pat. Off. . |
| 0212820 | 3/1987 | European Pat. Off. . |
| 339426 | 11/1989 | European Pat. Off. . |
| 1462133 | 1/1977 | United Kingdom . |
| 1462134 | 1/1977 | United Kingdom . |
| 139966 | 7/1985 | United Kingdom . |

OTHER PUBLICATIONS

Kochurovskaya, G. G. et al., Kriobiol. Kriomed., 3, 1977, pp. 76–79.

Turova, N. Y. et al., Chemical Reviews—Uspekhi Khimii, Mar. 1965, pp. 161–185.

Schick, M. J., Nonionic Surfactants, vol. 1, Marcel Dekker, Inc., New York (1967), pp. 28–41.

*Primary Examiner*—Paul J. Killos
*Attorney, Agent, or Firm*—R. M. Allen

[57] ABSTRACT

This invention relates to a process for the alkoxylation of a carboxylated compound comprising contacting the carboxylated compound with an alkylene oxide in the presence of a mixed metal oxide catalyst or a modified bimetallic or polymetallic catalyst under conditions effective to alkoxylate the carboxylated compound.

27 Claims, No Drawings

ALKOXYLATION OF CARBOXYLATED COMPOUNDS

RELATED APPLICATIONS

The following are related, commonly assigned applications, filed on an even date herewith:

U.S. patent application Ser. No. 07/585,457 and U.S. patent application Ser. No. 07/585,555; both of which are incorporated herein by reference.

BRIEF SUMMARY OF THE INVENTION

1. Technical Field

This invention relates to a process for the alkoxylation of a carboxylated compound comprising contacting the carboxylated compound with an alkylene oxide in the presence of a mixed metal oxide catalyst or a modified bimetallic or polymetallic catalyst under conditions effective to alkoxylate the carboxylated compound.

2. Background of the Invention

A variety of products such as surfactants, functional fluids, glycol ethers, polyols, and the like, are commercially prepared by the condensation reaction of alkylene oxides with organic compounds having at least one active hydrogen, generally, in the presence of an alkaline or acidic catalyst. The types and properties of the alkoxylation products depend on, among other things, the active hydrogen compound, the alkylene oxide, and the mole ratio of alkylene oxide to organic compound employed, as well as the catalyst. As a result of the alkoxylation, a mixture of condensation product species are obtained having a range of molecular weights.

In many applications of alkoxylated products, certain of the alkoxylation species provide much greater activity than others. Consequently, alkoxylation processes are desired that are selective to the production of those alkoxylation species. Further, for many of these uses, mixtures of alkoxylation products falling within a narrow range of molecular distribution of reacted alkylene oxide are believed to be superior to alkoxylation products in which a single alkoxylation specie predominates. For example, in a surfactant composition the range of materials on which the surfactant will be required to operate will normally vary. A range of alkoxylation species, even though narrow, will enhance the performance of the surfactant to the variety of materials which it may encounter. Further, mixtures of closely related alkoxylation species can provide a mixture having other improved properties such as in respect to cloud point, freezing point, pour point and viscosity as compared to a single specie. There, however, is a balance, and if the distribution of species becomes too broad, not only are less desirable alkoxylation species diluting the mixture, but also the more hydrophilic or lipophilic components than those in the sought range can be detrimental to the sought properties.

Moreover, a wide range of alkoxylation species can restrict the flexibility in ultimate product formulation using the alkoxylation reaction product. For example, in making oil-in-water emulsion products it is often desired to prepare a concentrated composition that minimizes the weight percent of water. This concentrate may then be diluted with water at the time of use, thereby saving the expense of shipping and storing water. The ability to form a desirable concentrate is generally dependent, in part, on having a narrow distribution of alkoxylation species since if heavier moieties are present, a greater portion of water is usually required otherwise gelling (evidencing product instability) may occur.

The recognition that certain distributions of moles of alkylene oxide to moles of organic compound in alkoxylation products can be important has long been recognized. For example, British Patent Specification No. 1,399,966 discloses the use of ethoxylates having a hydrophilic-lipophilic balance (HLB) of from about 10 to about 13.5 for use in a laundry detergent. In order to provide this HLB, the moles of ethylene oxide reacted per mole of fatty alcohol is described as being critical. In British Patent Specification No. 1,462,133, the sought cleaning composition employed alkylene oxide cosurfactants sufficient to provide even a narrower HLB, i.e., from about 10 to about 12.5. In British Specification No. 1,462,134, a detergent composition is disclosed which uses ethoxylates having an HLB of from about 9.5 to 11.5, with the preferred ethoxylates having an HLB of 10.0 to 11.1.

Thus, with the increased understanding of the properties to be provided by an alkoxylation product, greater demands are placed on tailoring the manufacture of the alkoxylation product to enhance the sought properties. Accordingly, efforts have been expended to provide alkoxylated products in which the distribution of reacted alkylene oxide units per mole of organic compound is limited to a range in which the sought properties are enhanced.

Alkoxylation processes are characterized by the condensation reaction in the presence of a catalyst of at least one alkylene oxide with at least one organic compound containing at least one active hydrogen. Perhaps the most common catalyst is potassium hydroxide. The products made using potassium hydroxide, however, generally exhibit a broad distribution of alkoxylate species. See, for example, M. J. Schick, *Nonionic Surfactants*, Volume 1, Marcel Dekker, Inc., New York, N.Y. (1967) pp. 28 to 41. That is, little selectivity to particular alkoxylate species is exhibited, especially at higher alkoxylation ratios. For example, FIG. 6 of U.S. Pat. No. 4,223,164 depicts the distribution of alkoxylate species prepared by ethoxylating a fatty alcohol mixture with 60 weight percent ethylene oxide using a potassium catalyst.

The distribution that will be obtained in alkoxylation processes can vary even using the same type of catalyst depending upon the type of organic compound being alkoxylated. For example, with nonylphenol, a Poisson-type distribution can be obtained using a potassium hydroxide catalyst. However, with aliphatic alcohols such as decanol, dodecanol, and the like, the distribution is even broader. These distributions are referred to herein as "Conventional Broad Distributions".

Acidic catalysts can also be used, and they tend to produce a narrower, and thus more desirable, molecular weight distributions; however, they also contribute to the formation of undesired by-products and, thus, are not in wide use commercially.

Particular emphasis has been placed on controlling molecular weight distribution of alkoxylation products. One approach has been to strip undesirable alkoxylate species from the product mixture. For instance, U.S. Pat. No. 3,682,849 discloses processes for the vapor phase removal of unreacted alcohol and lower boiling ethoxylate components. The compositions are said to contain less than about 1% of each of non-ethoxylated alcohols and monoethoxylates, less than 2% by weight of diethoxylates and less than 3% by weight of triethoxylates. This process results in a loss of raw materials since the lower ethoxylates are removed from the composition. Also, the stripped product still has a wide distribution of ethoxylate species, i.e., the higher molecular weight products are still present in the composition to a significant extent. To circumvent viscosity problems which would normally exist with straight-chain alcohols, about 20 to 30 percent of the starting alcohol is to be branched according to the patent.

Obtaining a narrower distribution of alkoxylated species at lower epoxide reactant to organic compound mole ratios can be readily accomplished. U.S. Pat. No. 4,098,818 discloses a process in which the mole ratio of catalyst (e.g., alkali metal and alkali metal hydride) to fatty alcohol is about 1:1. Ethoxylate distributions are disclosed for Parts C and D of Example 1 and are summarized as follows:

|  | Part C | Part D |
| --- | --- | --- |
| Primary fatty alcohol | 12 carbons | 12 to 14 carbons |
| Moles of ethylene oxide per mole of alcohol | 3.5 | 3 |
| Product molecular weight | 352 | 311 |
| Average ethoxylation | 3.8 | 2.54 |
| Distribution, % | | |
| $E_0$ | 0.7 | 3.8 |
| $E_1$ | 6.3 | 15.3 |
| $E_2$ | 17.3 | 25.9 |
| $E_3$ | 22.4 | 23.8 |
| $E_4$ | 21.2 | 15.9 |
| $E_5$ | 15.6 | 10.7 |
| $E_6$ | 8.6 | 3.5 |
| $E_7$ | 5.6 | 1.2 |
| $E_8$ | 2.3 | — |

The high catalyst content in combination with the low alkylene oxide to alcohol ratio appears to enable a narrow, low ethoxylate fraction to be produced. However, as the ratio of alkylene oxide to alcohol increases, the characteristic, Conventional Broad Distribution of alkali metal catalysts can be expected. Moreover, even though the disclosed process is reported to provide a narrower distribution of ethoxylate species, the distribution is skewed so that significant amounts of the higher ethoxylates are present. For example, in Part C, over 15 percent of the ethoxylate compositions had at least three more oxyethylene groups than the average based on the reactants, and that amount in Part D is over 16 percent.

European Patent Application No. A0095562, published Dec. 12, 1983, exemplifies the ability to obtain high selectivity to low ethoxylate species when low ratios of ethylene oxide reactant to alcohol are employed as well as the tendency to rapidly lose that selectivity when higher ethoxylated products are sought. For instance, Example 1, (described as a 1 mole EO adduct), which reports the use of a diethylaluminum fluoride catalyst, employs 300 grams of a 12 to 14 carbon alcohol and 64 grams of ethylene oxide and Example 5, (described as a 1.5 mole EO adduct) using the same catalyst, employs a weight ratio of alcohol to ethylene oxide at 300:118. Based on the graphically presented data, the distributions appear to be as follows:

|  | Example 1 | Example 5 |
| --- | --- | --- |
| $E_0$ | 27 | 10 |
| $E_1$ | 50 | 36 |
| $E_2$ | 17 | 33 |
| $E_3$ | 4 | 16 |
| $E_4$ | — | 6 |
| $E_5$ | — | 2 |
| $E_6$ | — | 1 |

Even with a small increase in ethoxylation from the described 1 mole EO adduct to the described 1.5 mole adduct, the distribution of ethoxylate species broadened considerably with more of the higher ethoxylates being produced as can be expected from a Conventional Broad Distribution. It may be that the catalyst is consumed in the reaction process so that it is not available to provide the narrower distributions of alkoxylation product mixtures at the high adduct levels.

Several catalysts have been identified that are reported to provide molecular weight distributions for higher ethoxylates that are narrower than those expected from a Conventional Broad Distribution. In particular, this work has emphasized ethoxylation catalysis by derivatives of the Group IIA alkaline earth metals. Interest in these catalysts, which to date has been confined almost exclusively to the production of non-ionic surfactants, stems from their demonstrated capability for providing hydrophobe ethoxylates having narrower molecular weight distributions, lower unreacted alcohol contents, and lower pour points than counterparts manufactured with conventional alkali metal-derived catalysts.

Yang and co-workers have been granted a series of U.S. patents which describe primarily the use of unmodified or phenolic-modified oxides and hydroxides of barium and strontium as ethoxylation catalysts for producing non-ionic surfactants exhibiting lower pour points, narrower molecular weight distributions, lower unreacted alcohol contents and better detergency than counterpart products prepared by state-of-the-art catalysis with alkali metal hydroxides. See U.S. Pat. Nos. 4,210,764; 4,223,164; 4,239,917; 4,254,287; 4,302,613 and 4,306,093. Significantly, these patents contain statements to the effect that the oxides and/or hydroxides of magnesium and calcium do not exhibit catalytic activity for ethoxylation, although they may function in the role of promoters for the barium and strontium compounds (U.S. Pat. No. 4,302,613).

The molecular weight distributions of the ethoxylates disclosed in these patents, while being narrower than conventional distributions, appear not to meet fully the desired narrowness. For example, FIG. 6 of U.S. Pat. No. 4,223,146 depicts the product distribution of an ethoxylate of a 12 to 14 carbon alcohol and 60 percent ethylene oxide using various catalysts. A barium hydroxide catalyst is described as providing a product mixture containing, as the most prevalent component, about 16 percent of the six mole ethoxylate. The distribution is, however, still relatively wide in that the ethoxylate species having three or more oxyethylene groups than the most prevalent component is above about 19 weight percent of the mixture and the distribution is skewed toward higher ethoxylates. The strontium hydroxide catalyst run which is also depicted on that figure appears to have a more symmetrical distribution but the most prevalent component, the seven mole ethoxylate, is present in an amount of about 14.5 weight percent and about 21 weight percent of the composition had three or more oxyethylene groups than the most prevalent component.

Also, U.S. Pat. No. 4,239,917 discloses ethoxylate distributions using barium hydroxide catalyst and a fatty alcohol. FIG. 7 of that patent illustrates the distribution at the 40 percent ethoxylation level with the four mole ethoxylate being the most prevalent component. Over about 19 weight percent of the mixture has three or more oxyethylene groups than the most prevalent component. FIG. 4 depicts the distribution of ethoxylation at the 65 percent ethoxylation level. The nine and ten mole ethoxylates are the most prevalent and each represent about 13 weight percent of the composition. The distribution is relatively symmetrical but about 17 weight percent of the composition has at least three more oxyethylene groups than the average peak (9.5 oxyethylene groups). Interestingly, comparative examples using sodium hydroxide catalyst are depicted on each of these figures and evidence the peaking that can be achieved with conventional base catalysts at low ethoxylation levels, but not at higher ethoxylation levels.

McCain and co-workers have published a series of European patent applications describing the catalytic use of basic salts of alkaline earth metals especially calcium, which are soluble in the reaction medium. These applications further disclose catalyst preparation procedures involving alcohol exchange in respect to the alkoxy moiety of the metal alkoxide catalytic species. See European Patent Nos. 0026544, 0026547 and 0026546, all herein incorporated by reference. These workers have also disclosed the use of strong acids to partially neutralize and thereby promote the catalytic action of certain alkaline earth metal derivatives. See U.S. Pat. No. 4,453,022 and U.S. Pat. No. 4,453,023 (barium-containing catalyst), both herein incorporated by reference.

The calcium-containing catalysts disclosed by McCain et al. provide enhanced selectivities to higher alkoxylate species as compared to mixtures produced using conventional potassium hydroxide catalyst. Indeed, bases exist to believe that these calcium-containing catalysts provide narrower distributions of alkoxylates than those provided by strontium- or barium-containing catalysts. However, there is still need for improvement in providing a narrower yet distribution of alkoxylation products, particularly a distribution in which at least one component constitutes at least 20 weight percent of the composition and alkoxylation products having more than three alkoxyl groups than the average peak alkoxylation component comprise very little of the product mixture.

U.S. Pat. Nos. 4,754,075, 4,886,917 and 4,820,673, herein incorporated by reference, relates to processes for preparing alkoxylation mixtures having relatively narrow alkoxylation product distributions using modified, calcium-containing catalysts. Processes are also disclosed for making alkoxylation catalysts using calcium oxide and/or calcium hydroxide as sources for the catalytically-active calcium. The alkoxylation product mixtures disclosed therein have a narrow and balanced distribution of alkoxylation species. The disclosed product mixtures are relatively free from large amounts of substantially higher alkoxylation moieties, i.e., those having at least three more alkoxyl groups than the average peak alkoxylate specie. It is stated therein that narrow distributions can be obtained where the most prevalent alkoxylation moiety has four or greater alkoxy units, that is, in the regions in which conventional catalysts provide a relatively wide range of alkoxylation species.

U.S. Pat. No. 4,902,658, herein incorporated by reference, relates to heterogeneous (organic polymer-supported) calcium-containing catalysts and the use thereof in the preparation of alkoxylation products, i.e., condensation reaction products of alkylene oxides and organic compounds having at least one active hydrogen. Processes are provided for preparing heterogeneous (organic polymer-supported) calcium-containing catalysts for alkoxylation using calcium oxide or calcium hydroxide as sources for the catalytically-active calcium. Alkoxylation products are provided that have beneficial, narrow molecular weight ranges and are essentially neutral in pH and free from catalyst residues.

Copending U.S. patent application Ser. No. 251,434, files Sep. 30, 1988, relates to modified calcium-containing catalysts and the use thereof in the preparation of alkoxylation products, i.e., condensation reaction products of alkylene oxides and organic compounds having at least one active hydrogen. Processes are provided for preparing modified calcium-containing catalysts for alkoxylation using calcium metal or a calcium-containing compound, e.g., calcium oxide or calcium hydroxide, as sources for the catalytically-active calcium and at least one divalent or polyvalent metal salt of an oxyacid as a modifier. Processes are also provided for preparing alkoxylation products that have beneficial, narrow molecular weight ranges using the modified calcium-containing catalysts.

Copending U.S. patent application Ser., No. 251,430, filed Sep. 30, 1988, (now U.S. Pat. No. 4,946,984) discloses the use of calcium sulfate as a catalyst in the preparation of alkoxylation products, i.e., condensation reaction products of alkylene oxides and organic compounds having at least one active hydrogen, that have beneficial, narrow molecular weight ranges.

Copending U.S. patent application Ser. No. 251,433, filed Sep. 30, 1988, describes modified calcium-containing bimetallic or polymetallic catalysts and the use thereof in the preparation of alkoxylation products, i.e., condensation reaction products of alkylene oxides and organic compounds having at least one active hydrogen. Processes are provided for preparing modified calcium-containing bimetallic or polymetallic catalysts for alkoxylation using calcium metal or a calcium-containing compound, e.g., calcium oxide or calcium hydroxide, as sources for the catalytically-active calcium. Processes are also provided for preparing alkoxylation products that have beneficial, narrow molecular weight ranges using the modified calcium-containing bimetallic or polymetallic catalysts.

Copending U.S. patent application Ser. No. 251,432, filed Sep. 30, 1988, relates to modified Group IIA metal-containing (other than calcium-containing) bimetallic or polymetallic catalysts and the use thereof in the preparation of alkoxylation products, i.e., condensation reaction products of alkylene oxides and organic compounds having at least one active hydrogen. Processes are provided for preparing the modified Group IIA metal-containing bimetallic or polymetallic catalysts for alkoxylation using a Group IIA metal or a Group IIA metal-containing compound, e.g., magnesium acetate, as sources for the catalytically-active Group IIA metal. Processes are also provided for preparing alkoxylation products that have beneficial, narrow molecular weight ranges using the modified Group IIA metal-containing bimetallic or polymetallic catalysts.

Copending U.S. patent application Ser. No. 251,436, filed Sep. 30, 1988, discloses modified Group IIIB metal-containing bimetallic or polymetallic catalysts and the use thereof in the preparation of alkoxylation products, i.e., condensation reaction products of alkylene oxides and organic compounds having at least one active hydrogen. Processes are provided for preparing the modified Group IIIB metal-containing bimetallic or polymetallic catalysts for alkoxylation using a Group IIIB metal or a Group IIIB metal-containing compound, e.g., lanthanum oxide, as sources for the catalytically-active Group IIIB metal. Processes are also provided for preparing alkoxylation products that have beneficial, narrow molecular weight ranges using the modified Group IIIB metal-containing bimetallic or polymetallic catalysts.

Copending U.S. pending application Ser. No. 251,431, filed Sep. 30, 1988, describes modified bimetallic or polymetallic (other than Groups IA, IIA and IIIB metals) catalysts and the use thereof in the preparation of alkoxylation products, i.e., condensation reaction products of alkylene oxides and organic compounds having at least one active hydrogen. Processes are provided for preparing the modified bimetallic or polymetallic catalysts for alkoxylation using a divalent or polyvalent metal or a divalent or polyvalent metal-containing compound, e.g., aluminum isopropoxide, as sources for the catalytically-active metal. Processes are also provided for preparing alkoxylation products that have beneficial, narrow molecular weight ranges using the modified bimetallic or polymetallic catalysts.

European Patent Application No. 339426 relates to an alkoxylation process in which an active hydrogen-containing compound is reacted with ethylene oxide or propylene oxide in the presence of calcined hydrotalcite to provide alkoxylated products having a narrow distribution of homologues.

U.S. Pat. No. 4,775,653 describes a process for preparing an alkoxylation catalyst in which the catalyst pre-mix is formed by admixing an alkoxylated alcohol with a calcium containing compound which is dispersible in the alkoxylated alcohol, an inorganic acid and an aluminum trialkoxide, the pre-mix being heated to a temperature and for a time sufficient to effect at least partial exchange reaction between the alkoxide groups of the aluminum alkoxide and the hydroxyl groups of the alkoxylated alcohol. There is also disclosed an alkoxylation process utilizing the catalysts formed as described above.

U.S. Pat. No. 4,892,977 discloses a process for preparing nonionic surfactants containing a narrow molecular weight distribution which comprises reacting a reactive hydrogen compound selected from the group consisting of monohydric alcohols having from about 6 to 30 carbon atoms with an alkylene oxide having from 2-4 carbon atoms at a temperature at which the reaction proceeds in the presence of at least a catalytic amount of a particular magnesium catalyst containing phosphorus.

Disclosure of the Invention

This invention relates to a process for the alkoxylation of a carboxylated compound comprising contacting the carboxylated compound with an alkylene oxide in the presence of a mixed metal oxide catalyst or a modified bimetallic or polymetallic catalyst under conditions effective to alkoxylate the carboxylated compound.

The alkoxylates of carboxylated compounds prepared in accordance with the process of this invention can exhibit a narrow distribution of alkoxylate species as more fully described hereinafter.

In a preferred embodiment, the process of this invention can provide alkoxylates of carboxylated compounds having a selected amount of alkoxylation. In particular, the process of this invention can selectively provide low mole alkoxylates of carboxylated compounds such as one mole ethoxylates, two mole ethoxylates and the like. Preferably, a carboxylated fatty alcohol can be alkoxylated to selectively provide a low mole alkoxylate of the carboxylated fatty alcohol under the process conditions described herein. The carboxylated fatty alcohol low mole alkoxylate can then be hydrolyzed or transesterified to give a low mole alkoxylate of the fatty alcohol.

The alkoxylates of carboxylated compounds prepared by the process of this invention are useful for a wide variety of applications. In particular, the alkoxylates of carboxylated compounds are useful as chemical intermediates which can undergo decarboxylation to afford dialkyl ethers of (poly)ethylene glycols, e.g., SELEXOL® materials, such as monoethylene glycol dimethyl or diethyl ether (glyme and ethyl glyme), diethylene glycol dimethyl or diethyl ether (diglyme and ethyl diglyme), triethylene glycol dimethyl or diethyl ether (triglyme and ethyl triglyme), tetraethylene glycol dimethyl or diethyl ether (tetraglyme and ethyl tetraglyme), polyethylene glycol dimethyl or diethyl ethers (polyglymes and ethyl polyglymes) and the like. The alkoxylates of carboxylated compounds can also be hydrolyzed or transesterified to afford surfactant materials, e.g., TERGITOL® nonionic surfactants, polyoxyalkylene glycol materials, e.g., CARBOWAX® poly(oxyethylene)glycols and POLYOX® poly(oxyethylene)glycols, poly(oxyethylene)-(oxypropylene)-glycol materials, UCON® fluids and lubricants, CARBITOL® materials, e.g., 2-(2-methoxyethoxy)ethanol, CELLOSOLVE® materials, e.g., 2-methoxyethanol, and the like with no by-product salt formation.

DETAILED DESCRIPTION

As indicated above, this invention relates to a process for the alkoxylation of a carboxylated compound comprising contacting the carboxylated compound with an alkylene oxide in the presence of a mixed metal oxide catalyst or a modified bimetallic or polymetallic catalyst under conditions effective to alkoxylate the carboxylated compound.

Suitable carboxylated compounds which can be employed in the reaction include any permissible substituted or unsubstituted carboxylated compound(s), including substituted and unsubstituted esters, carbonic acid esters, carbamic acid esters and the like, such as those embraced by the formulae $ROC(O)R_1$, $ROC(O)R_2$, $ROC(O)OR_1$, $ROC(O)OR_2$, $RN(C(O)OR_1)R$ or $RN(C(O)OR_2)R$ wherein R is the residue of an organic compound, $R_1$ is the residue of an organic compound and $R_2$ is the residue of an organic compound. It is understood that the R and $R_1$ substituents together, the R and $R_2$ substituents together, and the R substituents together can complete a cycloalkyl ring or a heterocycloalkyl ring which can be substituted or unsubstituted. Illustrative carboxylated compounds include, for example, methyl acetate, dimethyl carbonate, diethyl carbonate, dodecyl acetate, N,N-dimethylamino acetate, methyl 1-piperazine carboxylate, ethyl 1-piperazine carboxylate, bis(2-methoxyethyl)-carbonate, bis[2-(2-methoxyethoxy)ethyl]carbonate, diallyl acetate, fatty alcohol acetate, nonyl phenol acetate, diphenyl carbonate and the like.

The alkylene oxides which provide the oxyalkylene units in the carboxylated compound include any permissible alkylene oxide(s) such as ethylene oxide, propylene oxide, 1,2-butylene oxide, 2,3-butylene oxide, 1,2- and 2,3-pentylene oxide, cyclohexylene oxide, 1,2-hexylene oxide, 1,2-octylene oxide, and 1,2-decylene oxide; epoxidized fatty alcohols such as epoxidized soybean fatty alcohols and epoxidized linseed fatty alcohols; aromatic epoxides such as styrene oxide and 2-methylstyrene oxide; and hydroxy- and halogen-substituted alkylene oxides such as glycidol, epichlorhydrin and epibromhydrin. The preferred alkylene oxides are ethylene oxide, propylene oxide or mixtures thereof. The molar ratio of alkylene oxide to carboxylated compound is not narrowly critical and can vary over a wide range, for example, from about 0.5:1 or less to about 1000:1 or greater.

Suitable catalysts which can be employed in the process of this invention include two or more metal oxides. A magnesium:aluminum mixed metal oxide is a preferred mixed metal oxide catalyst as more fully described below. Both homogeneous and heterogeneous catalysts can be employed in the reaction. The amount of catalyst used in the reaction is not narrowly critical and is dependent on whether the reaction is conducted batchwise or continuously. If batchwise, the catalyst employed can range from about 0.01 weight percent or less to about 10 weight percent or greater of the total weight of the starting materials. If continuously, generally a fixed bed is employed.

Suitable catalysts for use in the process of this invention comprise mixed metal oxides containing two or more metal oxides. Illustrative of such mixed metal oxides include, for example, two or more of the following: Group IA metal oxides, Group IIA metal oxides, Group IIIB metal oxides (including lanthanides and actinides), Group IVB metal oxides, Group VB metal oxides, Group VIB metal oxides, Group VIIB metal oxides, Group VIII metal oxides, Group IB metal oxides, Group IIB metal oxides, Group IIIA metal oxides, Group IVA metal oxides, Group VA metal oxides or Group VIA metal oxides. Preferred mixed metal oxides are amphoteric or basic. Preferred mixed metal oxides which may be utilized as catalysts include, for example, two or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth.

Group IIA metal oxides such as magnesium oxide and calcium oxide and Group IIIA metal oxides such as aluminum oxide and gallium oxide are preferred mixed metal oxides for use in this invention. For mixed metal oxides in which at least one of the metals is magnesium, suitable metals in association with magnesium may include, for example, one or more of the following: Group IIIA metals such as boron, aluminum, gallium and indium, Group IIIB metals such as scandium, yttrium and lanthanum including the lanthanides, Group VB metals such as niobium and tantalum, Group VIB metals such as chromium, molybdenum and tungsten, Group VIII metals such as iron, cobalt and nickel, Group IIB metals such as zinc and cadmium, Group IVA metals such as silicon, germanium, tin and lead, Group VA metals such as arsenic, antimony and bismuth, and Group IVB metals such as zirconium and hafnium. For mixed metal oxides in which at least one of the metals is calcium, suitable metals in association with calcium may include, for example, one or more of the following: Group IIIA metals such as boron, aluminum, gallium and indium, Group IVA metals such as silicon, germanium, tin and lead, Group VB metals such as niobium and tantalum, and Group VIB metals such as chromium, molybdenum and tungsten.

Illustrative of mixed metal oxides which may be used as catalysts include, for example, $MgO\text{-}Al_2O_3$, $MgO\text{-}SiO_2$, $MgO\text{-}CdO$, $MgO\text{-}Bi_2O_3$, $MgO\text{-}Sb_2O_5$, $MgO\text{-}SnO_2$, $MgO\text{-}ZrO_2$, $MgO\text{-}BeO$, $MgO\text{-}TiO_2$, $MgO\text{-}CaO$, $MgO\text{-}SrO$, $MgO\text{-}ZnO$, $MgO\text{-}Ga_2O_3$, $MgO\text{-}Y_2O_3$, $MgO\text{-}La_2O_3$, $MgO\text{-}MoO_3$, $MgO\text{-}Mn_2O_3$, $MgO\text{-}Fe_2O_3$, $MgO\text{-}Co_3O_4$, $MgO\text{-}WO_3$, $MgO\text{-}V_2O_5$, $MgO\text{-}Cr_2O_3$, $MgO\text{-}ThO_2$, $MgO\text{-}Na_2O$, $MgO\text{-}BaO$, $MgO\text{-}CaO$, $MgO\text{-}HfO_2$, $MgO\text{-}Li_2O$, $MgO\text{-}Nb_2O_5$, $MgO\text{-}Ta_2O_5$, $MgO\text{-}Gd_2O_3$, $MgO\text{-}Lu_2O_3$, $MgO\text{-}Yb_2O_3$, $MgO\text{-}CeO_2$, $MgO\text{-}Sc_2O_3$, $MgO\text{-}PbO$, $MgO\text{-}NiO$, $MgO\text{-}CuO$, $MgO\text{-}CoO$, $MgO\text{-}B_2O_3$, $CaO\text{-}SiO_2$, $CaO\text{-}Al_2O_3$, $CaO\text{-}SnO$, $CaO\text{-}PbO$, $CaO\text{-}Nb_2O_5$, $CaO\text{-}Ta_2O_5$, $CaO\text{-}Cr_2O_3$, $CaO\text{-}MoO_3$, $CaO\text{-}WO_3$, $CaO\text{-}TiO_2$, $CaO\text{-}HfO_2$, $MgO\text{-}SiO_2\text{-}Al_2O_3$, $MgO\text{-}SiO_2\text{-}ZnO$, $MgO\text{-}SiO_2\text{-}ZrO_2$, $MgO\text{-}SiO_2\text{-}CuO$, $MgO\text{-}SiO_2\text{-}CaO$, $MgO\text{-}SiO_2\text{-}Fe_2O_3$, $MgO\text{-}SiO_2\text{-}B_2O_3$, $MgO\text{-}SiO_2\text{-}WO_3$, $MgO\text{-}SiO_2\text{-}Na_2O$, $MgO\text{-}SiO_2\text{-}Ga_2O_3$, $MgO\text{-}SiO_2\text{-}La_2O_3$, $MgO\text{-}SiO_2\text{-}Nb_2O_5$, $MgO\text{-}SiO_2\text{-}Mn_2O_3$, $MgO\text{-}SiO_2\text{-}Co_3O_4$, $MgO\text{-}SiO_2\text{-}NiO$, $MgO\text{-}SiO_2\text{-}PbO$, $MgO\text{-}SiO_2\text{-}Bi_2O_3$, $MgO\text{-}Al_2O_3\text{-}ZnO$, $MgO\text{-}Al_2O_3\text{-}ZrO_2$, $MgO\text{-}Al_2O_3\text{-}Fe_2O_3$, $MgO\text{-}Al_2O_3\text{-}WO_3$, $MgO\text{-}Al_2O_3\text{-}La_2O_3$, $MgO\text{-}Al_2O_3\text{-}Co_3O_4$, $CaO\text{-}SiO_2\text{-}Al_2O_3$, $CaO\text{-}SiO_2\text{-}SnO$, $CaO\text{-}SiO_2\text{-}Nb_2O_5$, $CaO\text{-}SiO_2\text{-}WO_3$, $CaO\text{-}SiO_2\text{-}TiO_2$, $CaO\text{-}SiO_2\text{-}MoO_3$, $CaO\text{-}SiO_2\text{-}HfO_2$, $CaO\text{-}SiO_2\text{-}Ta_2O_5$, $CaO\text{-}Al_2O_3\text{-}SiO_2$, $CaO\text{-}Al_2O_3\text{-}PbO$, $CaO\text{-}Al_2O_3\text{-}Nb_2O_5$, $CaO\text{-}Al_2O_3\text{-}WO_3$, $CaO\text{-}Al_2O_3\text{-}TiO_2$, $CaO\text{-}Al_2O_3\text{-}MoO_3$, $CaO\text{-}HfO_2\text{-}Al_2O_3$, $CaO\text{-}HfO_2\text{-}TiO_2$, and the like. Other suitable mixed metal oxides embraced within the scope of this invention are disclosed by Tanabe et al., Bulletin of the Chemical Society of Japan, Vol. 47(5), pp. 1064–1066 (1974).

The mixed metal oxides described herein which can be used as catalysts may contribute to product selectivity and/or catalytic activity of the reaction and/or stability of the catalyst. As discussed hereinafter, the catalyst employed in this invention may also contain support(s), binding agent(s) or other additives to stabilize or otherwise help in the manufacture of the catalyst.

The catalysts which comprise two or more metal oxides may be prepared in a wide variety of ways. For example, the two or more metal oxides can be provided from metal salts which can either be heated or precipitated to form the mixed metal oxides. Also, two or more metal oxides may be provided as a partial condensate on a support, such as a silica or alpha, beta or gamma alumina, silicon carbide, and the like, and then condensed by heating to effect polymerization to the desired oxide form. The two or more metal oxides may be condensed from hydrolyzable monomers to the desired oxides, indeed, to form oxide powders which can thereafter be compressed in the presence of a condensation catalyst to form pellets and larger structures of the mixed metal oxide catalyst. A blend of the powders and condensation catalyst can be made into a shapeable paste which can be extruded and cut into pellets according to conventional procedures. The extrudate may thereafter be fired to cure the condensation catalyst and fix the structure. The cut extrudate may be blended with a support material such as those characterized above, and the blend fired to fuse the mixed metal oxide catalyst to the support.

In an embodiment of this invention, a magnesium salt, e.g., magnesium nitrate, and an aluminum salt, e.g., aluminum nitrate, are precipitated using ammonium hydroxide. The material is then washed with deionized water and calcined at a temperature of from about 350° C. to about 450° C. to afford the desired magnesium:aluminum mixed metal oxide catalyst.

In another embodiment, a magnesium oxide, e.g., magnesium carbonate hydroxide pentahydrate, and an aluminum oxide, e.g., aluminum hydroxide hydrate, are added to deionized water and thoroughly mixed to form a paste. The paste is then calcined at a temperature of from about 350° C. to about 450° C. to afford the desired magnesium:aluminum mixed metal oxide catalyst.

A preferred catalyst structure comprises a Group IIA and IIIA mixed metal oxide having a surface area of at least about 100 m²/gm which may or may not be bonded to a support material. The catalysts on a support preferably have a surface area greater than about 20 m²/gm to as high as about 260 m²/gm, or greater depending upon which metal oxides are employed. In the case of magnesium:aluminum oxides, the surface area can be greater than about 50 m²/gm to as high as about 260 m²/gm, more preferably, greater than about 100 m²/gm to as high as about 260 m²/gm, determined according to the single point $N_2$ method.

The term "support," as used herein and in the claims, means a solid structure which does not adversely affect the catalytic properties of the catalyst and is at least as stable as the catalyst to the reaction medium. The support can function as a catalyst independent of the mixed metal oxide catalyst used herein, although it may have lower catalytic activity to the reaction. The support may act in concert with the catalyst to moderate the reaction. Some supports may contribute to the selectivity of the reaction. The catalyst structure can comprise from about 2 to about 60 percent by weight or greater of the support, more preferably from about 10 to about 50 percent by weight of the support, the remainder being the weight of the mixed metal oxides. Included in the weight of the support is the weight of any binding agent such as phosphates, sulfates, silicates, fluorides, and the like, and any other additive provided to stabilize or otherwise help in the manufacture of the catalyst. The support may be particles as large or larger than the catalyst component and "glued" to the catalyst by virtue of a binding medium.

The support may constitute a separate phase in the process of extruding the catalytic structure. In this embodiment, the support forming material, preferably as a paste is blended with a paste of the catalyst or a partial condensate thereof. The paste may comprise the oxide forms of the support and the catalyst, each blended with water, and/or binding agents. The extrudate of the blend is passed through a multiorificed die and chopped into pellets of the desired sizes. The particles may be doughnut shaped, spherical, and the like. Then the particles are calcined to dry them and complete any condensation reaction in the support and/or the mixed metal oxide catalyst.

A preferred group of mixed metal oxide catalysts for use in this invention include materials having the formula:

$$M_x{}^{2+}Q_y{}^{3+}(OH)_{2x+3y-nz}A_z{}^{n-}\cdot a\ H_2O \qquad (I)$$

wherein M is at least one divalent metal cation; Q is at least one trivalent metal cation; and A is at least one anion providing a valence (n−), wherein n is at least 1, e.g., between 1 and 4 and most often between 1 and 3, and wherein a is a positive number, M, Q, and A are provided in a proportion such that x/y is a number equal to or greater than 1, z has a value greater than zero and $2x+3y-nz$ is a positive number. M, Q and A may be selected to provide a layered structure. Preferably, x/y is in the range of 1 to 12, more preferably x/y is in the range of 1 to 6 and most preferably is in the range of 1 to 4. Preferably, z has a value such that x/z is between n and 12n, more preferably between n and 6n and most preferably between n and 4n.

Suitable divalent metal cations, M, broadly include elements selected from the Transition elements and Groups IIA and IVA of the Periodic Table as well as certain Group IIIB elements. As specific examples can be mentioned magnesium, calcium, titanium, vanadium, chromium, manganese, iron, cobalt, nickel, palladium, platinum, copper, zinc, cadmium, mercury, tin and lead. Divalent metal cations which are particularly suitable are magnesium, nickel, cobalt, zinc, calcium, strontium and copper. Suitable trivalent metal cations, Q, broadly include elements selected from the Transition elements and Groups IIIA and VA of the Periodic Table as well as certain Group IIIB elements. As specific examples can be mentioned aluminum, antimony, titanium, scandium, bismuth, vanadium, yttrium, chromium, iron, manganese, cobalt, ruthenium, nickel, gold, gallium, thallium, and cerium. Trivalent metal cations which are particularly suitable can be selected from aluminum, boron, gallium and lanthanum.

The composition of formula (I) also can include a wide range of anions, A. Any anion or combination of anions which can balance the charge of the cations can be used. Suitable anions include inter alia, halides (such as chloride, fluoride, bromide, and iodide), nitrite, nitrate, sulfite, sulfate, sulfonate, carbonate, chromate, cyanate, phosphite, phosphate, molybdocyanate, bicarbonate, hydroxide, arsenate, chlorate, ferrocyanide, borate, cyanide, cyanaurate, cyanaurite, ferricyanide, selenate, tellurate, bisulfate, as well as organic anions such as oxalate, acetate, hexanoate, sebacate, formate, benzoate, malonate, lactate, oleate, salicylate, stearate, citrate, tartrate, maleate, and the like. The class of metalate anions described in U.S. Pat. No. 4,667,045, including metavanadate, orthovanadate, molybdate, tungstate, hydrogen pyrovanadate and pyrovanadate, also are suitable as anion A. Anions suitable for use in combination with the metal cations previously identified as being particularly suitable are carbonate, halide, phosphate, chromate, sulfate, hydroxide, oxalate, acetate, nitrate, hexanoate, sebacate, vanadate, molybdate, tungstate and ferrocyanate.

The foregoing lists of suitable divalent and trivalent cations and suitable anions are meant to be illustrative and not exclusive. Those skilled in the art will recognize that other cations and anions can be used provided that the specific type of cations and their relative amounts (x/y ratio) and the specific type of anions and their relative amount result in a mixed metal oxide composition.

Included in the materials identified above are those based on exchangeable anionic clay minerals. For example, compositions of formula (I) wherein M is magnesium and Q is aluminum are related to hydrotalcites, while compositions in which M is nickel and A is aluminum are related to takovites. In fact, mixed metal oxides prepared using magnesium, nickel or cobalt as the divalent cation and aluminum as the trivalent cation exhibit the typical X-ray diffraction pattern of a hydrotalcite.

In another preferred aspect, the process of this invention can utilize mixed metal oxide catalyst compositions prepared by calcining at an elevated temperature compositions according to formula (I). Suitable calcined compositions have the general formula:

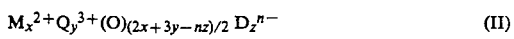
$$M_x^{2+} Q_y^{3+} (O)_{(2x+3y-nz)/2} D_z^{n-} \qquad (II)$$

wherein M, Q, x, y, z and n have the same meanings defined above in connection with formula (I), and D is at least one nonvolatile anion. Nonvolatile anions may include, inter alia, halides, nitrates, phosphites, phosphate, vanadate, molybdate, tungstate, sulfite, sulfate, chromate, arsenate, borate, chlorate and the like. This list is illustrative and not exclusive.

Heat treating the formula (I) compositions to prepare the calcined mixed metal oxide compositions of formula (II) can be done, for example, at a temperature in the range of 200° C. to 800° C. for a period of time of about 12 to 24 hours under an inert atmosphere such as nitrogen or in appropriate cases under an oxidizing atmosphere such as air.

Calcination of the mixed metal oxide composition dehydrates the composition and converts at least partially the metal hydroxides to metal oxides. Any nonvolatile anions may be present in the calcined material.

Provided the calcination temperature is not excessive, the mixed metal oxide can be rehydrated to the mixed metal hydroxide with water. Generally, the mixed metal oxide can be restored readily if the calcination temperature does not exceed about 600° C. Mixed metal oxides which are calcined under more severe conditions are not easily rehydrated and lower surface area materials are obtained.

Certain compositions falling within formula (I), such as hydrotalcite, which comprises a magnesium-aluminum hydroxide carbonate, and takovite, which comprises a nickel-aluminum hydroxide carbonate, are naturally occurring compositions. However, such compounds, as well as their related compositions, also can be prepared synthetically from inexpensive starting materials using well-known coprecipitation techniques. Procedures for direct synthesis of such materials are described in Itaya et al., *Inorg. Chem.* (1987) 26:624–626; Taylor, R. M., *Clay Minerals* (1984) 19:591–603; Reichle, U.S. Pat. No. 4,476,324; Bish, D. L., *Bull. Mineral* (1980), 103:170–175 and Miyata et al., *Clays and Clay Minerals* (1977), 25:14–18. Using direct synthesis one has the ability to vary within wide limits the $M^{+2}/Q^{+3}$ atomic ratio as well as the anion.

For example, a composition of formula (I) where $M^{+2}$ is nickel or magnesium, $Q^{+3}$ is aluminum and $A^{n-}$ is carbonate can be prepared by adding, as aqueous solutions, (a) a mixture of nitrates, sulfates or chlorides of nickel or magnesium and aluminum in a desired atomic ratio of nickel or magnesium to aluminum, e.g. 6 atoms of nickel as nickel chloride to 2 atoms of aluminum as aluminum chloride, to (b) an aqueous solution of a stoichiometric amount of sodium hydroxide and a water soluble salt of the desired anion, e.g., sodium carbonate. The two solutions are mixed at a temperature of about 25° C. to 35° C. with vigorous stirring over a several-hour period to produce a slurry. The slurry then is heated for about 18 hours at a temperature within the range of about 50° C. to 200° C. (preferably between about 60° C. to 75° C.) in order to control crystallization and the ultimate particle size of the resulting crystals. After filtering, and thorough washing and drying, the solids are recovered, typically as a powder.

As noted above, this procedure can be adapted to a wide variety of cations, cation atomic ratios and anion substitutions. For example, water soluble salts of divalent magnesium, cobalt, zinc, copper, iron and calcium can be substituted for the nickel chloride illustrated above, while water soluble salts of trivalent gallium and lanthanum can replace the aluminum chloride. A wide variety of other combinations also will be apparent to those skilled in the art. Generally, the rate of metal ion addition to the aqueous caustic/anion solution is not critical and can be varied widely. For example, a preferred preparation method is described in Schaper, H. et al., *Applied Catalysis*, 54, 1989, 79–90, the disclosure of which is incorporated herein by reference. The reaction temperature also is not critical, although the temperature during the reaction preferably is kept below about 100° C. An important feature of the procedure is the use of efficient agitation during the mixing procedure to avoid the formation of undesired by-products.

Loading of an anion A or D into the mixed metal oxide compositions is influenced by a variety of factors including (i) the amount of anion used in the preparation relative to the metal cations, (ii) the atomic ratio of the metal cations (x/y) in the preparation procedure, (iii) the size of the cations and anions and (iv) the preparation procedure. As used herein, "loading" is defined as the amount of available valences provided by a desired anion A or D expressed as a percentage of the total available valences for anion A or D. For example, carbonate loading in a hydrotalcite-type catalyst can be maximized by (i) using an excess (e.g., a greater than 3:1 molar ratio) of sodium carbonate to aluminum chloride during catalyst preparation and (2) adjusting the atomic ratio of magnesium to aluminum cations to about 2:1.

Mixed metal oxide compositions suitable as catalysts also can be prepared from the native or synthetic hydrotalcite-type compositions by ion exchange. For example, hydrotalcite can be treated at ambient conditions with 0.01N phosphoric acid for about 18 hours to replace the carbonate anion with phosphate anion. A halide analog of hydrotalcite prepared directly or by anion-exchange could be contacted with molybdic acid or a water soluble salt thereof, or with a water soluble salt of tungstic acid or vanadic acid in order to substitute the transition metal anion for the halide anion in the catalyst structure thereby to produce a mixed metal oxide composition of formula (I). Other ion exchanges will be apparent to those skilled in the art.

Calcined mixed metal oxide compositions may exhibit a higher level of selectivity/activity than uncalcined compositions. If a calcined mixed metal oxide catalyst composition experiences any decline in selectivity, it can be regenerated by a heat treatment in the presence of air to restore at least a portion of its initial level of selectivity/activity enhancement and reused. Conditions discussed above for calcining the hydrated mixed metal oxide compositions are suitable for regenerating compositions which have experienced a decline in activity.

Catalysts having the formulas (I) and (II) above wherein M is at least one of magnesium and calcium, Q is aluminum or gallium, A is at least one of carbonate, bicarbonate, phosphate, sulfate and nitrate, x/y is between 1 and 20, z has a value which satisfies the relationship: x/z is between n and 12n, and a is a positive number, are generally preferred for vapor phase decarboxylation due to their combination of activity (conversion of precursor) and selectivity. A preferred process involves a vapor phase process using mixed metal oxide catalyst wherein $M^{2+}$ is magnesium, $Q^{3+}$ is aluminum, $A^{n-}$ is carbonate, x/y is about 1, and z is about 1.

A group of preferred mixed metal oxide catalyst compositions which can be employed in the process of this invention is disclosed in copending U.S. patent application Ser. No. 125,134, filed Nov. 25, 1987, the disclosure of which is incorporated herein by reference.

The modified bimetallic or polymetallic catalysts useful in this invention comprise one or more metal-containing compounds which are modified with an organic or inorganic oxyacid having a divalent or polyvalent anion such as sulfuric acid, phosphoric acid, carbonic acid, pyrosulfuric acid and the like, or by metal salts of organic or inorganic oxyacids having divalent or polyvalent anions such as aluminum sulfate, zinc sulfate, zinc phosphate and the like or mixtures thereof. These modified catalysts are believed to have complex structures which are probably comprised of a mixture of species, certain of which may not even be catalytically active. Those species which are catalytically active are believed to have structures of the type depicted by the following formula:

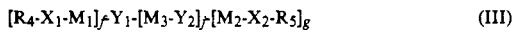

$$[R_4-X_1-M_1]_f-Y_1-[M_3-Y_2]_j-[M_2-X_2-R_5]_g \qquad (III)$$

wherein:

$R_4$ and $R_5$ are independently hydrogen or the residue of an organic compound having at least one active hydrogen;

$X_1$ and $X_2$ are independently oxygen, sulfur or nitrogen;

$M_1$, $M_2$ and $M_3$ are independently a divalent or polyvalent metal;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum f+g is equal to the valence of $Y_1$ when j is a value of 0, and f and g are integers having a value such that the sum f+g is equal to the valence of $Y_1$ plus $[M_3-Y_2]_j$ when j is a value other than 0. It is understood that the above catalyst formula is speculation only.

The modifier of the catalyst is a divalent or polyvalent acid or a divalent or polyvalent metal salt of an oxyacid or mixtures thereof and contains at least one, most often at least about 2, oxygen atoms that are conventionally depicted as double bonded to the nucleus atom. Such acids and metal salts include, for example, sulfuric and phosphoric acid and the sulfates and phosphates of zirconium, zinc and aluminum.

The types of divalent and polyvalent anions of oxyacids and metal salts of oxyacids suitable for use in this invention, e.g., $Y_1$ and $Y_2$, include by way of example only, sulfates, e.g., $SO_4^{-2}$, phosphates, e.g., $PO_4^{-3}$, manganates, e.g., $MnO_4^{-2}$, titanates, e.g., $TiO_3^{-2}$, tantalates, e.g., $Ta_2O_6^{-2}$, molybdates, e.g., $MoO_4^{-2}$, vanadates, e.g., $V_2O_4^{-2}$, chromates, e.g., $CrO_4^{-2}$, zirconates, e.g., $ZrO_3^{-2}$, polyphosphates and the like.

Illustrative of metals which may be included in the divalent or polyvalent metal salt modifier and also in the bimetallic and polymetallic catalysts include calcium, magnesium, strontium, barium, lanthanum, titanium, zirconium, hafnium, vanadium, niobium, tantalum, chromium, molybdenum, tungsten, manganese, iron, cobalt, nickel, copper, zinc, cadmium, mercury, boron, aluminum, gallium, indium, thallium, carbon, silicon, germanium, tin, lead, phosphorus, arsenic, antimony, sulfur, selenium and tellurium. Calcium or calcium in combination with a bivalent or polyvalent metal are preferred metals for the modified bimetallic and polymetallic catalysts.

In general, at the time of modification, the catalyst precursor composition may be represented by the following formula:

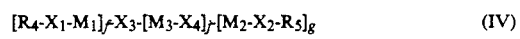

$$[R_4-X_1-M_1]_f-X_3-[M_3-X_4]_j-[M_2-X_2-R_5]_g \qquad (IV)$$

wherein $R_4$, $R_5$, $X_1$, $X_2$, $M_1$, $M_2$, $M_3$, and j are as defined hereinabove for formula (III), $X_3$ and $X_4$ are independently oxygen, sulfur or nitrogen, and f and g are integers having a value such that the sum f+g is equal to the valence of $X_3$ when j is a value of 0, and f and g are integers having a value such that the sum of f+g is equal to the valence of $X_3$ plus $[M_3-X_4]_j$ when j is a value other than 0. $R_4$ and $R_5$ independently may also contain double bonded oxygen (the organic compound was a carboxylic acid), heteroatom such as oxygen, sulfur, nitrogen and phosphorous (e.g., the organic compound was a glycol, polyamine, ether of a glycol or the like). Frequently, $R_4$ and $R_5$ may comprise 1 to 20 carbons. It is understood that the above catalyst precursor formula is speculation only.

For purposes of this invention including the claims hereinafter, it is understood that the catalyst precursor formula shall be inclusive of polyvalency requirements for $M_1$, $M_2$ and $M_3$ and that such polyvalency requirements are appropriately satisfied in the formula. It is also understood that any polyvalency requirements of $M_3$ may be satisfied by $R_4-X_1-$ or $R_5-X_2-$.

The preparation of modified bimetallic and polymetallic catalysts is characterized by a considerable degree of operational latitude. A preferred preparation involves the following steps:

Step 1—Reaction of a divalent or polyvalent metal or a metal-containing compound with a suitable first organic compound having at least one active hydrogen to produce a first divalent or polyvalent metal-containing composition.

Step 2—Reaction of a divalent or polyvalent metal or other suitable source of divalent or polyvalent metal with a suitable second organic compound containing at least one active hydrogen to produce a second divalent or polyvalent metal-containing composition.

Step 3—Reaction of the first divalent or polyvalent metal-containing composition with the second divalent or polyvalent metal-containing composition to produce the catalyst precursor composition.

Step 4—Reaction of the catalyst precursor composition with a suitable third organic compound having at least one active hydrogen optionally to effect exchange of the first and/or second organic compound-derived organic radicals for the third organic compound-derived organic radicals.

During or following the exchange reactions of step 4, the first and/or second organic compounds, which preferably are substantially more volatile than the third organic compound, are removed from the system by distillation. At the conclusion of this operation, the unmodified version of the catalyst is obtained in the form of a residue-free slurry in the third organic compound.

In the preparation of the intermediate unmodified form of the bimetallic or polymetallic catalyst, steps 1 and 2 may be combined into one operation. The first and second divalent or polyvalent metal-containing compositions prepared in steps 1 and 2 may be the same compositions, thereby omitting step 2. Additionally, steps 1 and 4 above may be combined into one operation wherein the divalent or polyvalent metal or the divalent or polyvalent metal-containing compound is reacted with a mixture of a suitable first and third organic compounds. Alternatively, step 2 may be omitted and a divalent or polyvalent metal salt of an oxyacid used in step 5 below. The procedure of combining steps 1 and 4 may be employed because it tends to minimize color build-up in the catalyst slurry. From the standpoint of the final product characteristics, both procedures are equally acceptable. Modified processes wherein the first organic compound is fed into a slurry of the third organic compound and the divalent or polyvalent metal base or the third organic compound is fed into a slurry (or, in some cases, a solution) of the divalent or polyvalent metal base in the first organic compound are also operationally viable, although their use offers no perceived advantage over the batch-charging version.

The preparation of the modified catalyst involves a fifth processing step which, like that of steps 1 through 4, is a distinct step in terms of the chemistry which takes place.

Step 5—Treatment of the slurry of unmodified catalyst in the third organic compound with a deficiency of some appropriate modifier such as a divalent or polyvalent oxyacid or a divalent or polyvalent metal salt of an oxyacid or mixtures thereof.

This step provides a highly-active, modified bimetallic or polymetallic catalyst in the form of a slurry in the third organic compound.

Preferred bimetallic and polymetallic catalysts for use in this invention are described in U.S. Pat. No. 4,820,673, U.S. Pat. No. 4,754,075 U.S. Pat. No. 4,886,917, and copending U.S. patent application Ser. No. 298,897, filed Jan. 18, 1989, all of which are incorporated herein by reference. Other preferred bimetallic and polymetallic catalysts for use in this invention are described in copending U.S. patent application Ser. Nos. 251,434, 251,430, 251,433, 251,432, 251,436 and 251,431, all filed Sep. 30, 1988, and all incorporated herein by reference.

While the exact catalytic mechanism is not fully appreciated, it is believed that the mixed metal oxide catalyst and the modified bimetallic or polymetallic catalyst generate metal alkoxide species on the catalyst surface under the process conditions described herein. The metal alkoxide species are capable of being alkoxylated and ultimately incorporated into the carboxylated compound, for example by transesterification, to provide the desired alkoxylates of carboxylated compounds.

The process of this invention can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the reaction at reduced pressures of from about 1 mm Hg to less than about 760 mm Hg. The reaction is preferably effected in the liquid or vapor or supercritical liquid states or mixtures thereof. The pressure should be sufficient so as to not allow decarboxylation.

The temperature of the process of this invention may be as low as about ambient temperature to about 300° C. Preferably, the reaction temperature ranges from about 50° C. to about 200° C., and most preferably from about 60° C. to about 120° C. The temperature should be sufficient so as to not allow decarboxylation.

The process of this invention can be conducted in the presence of an inert diluent which can be either a liquid or gas. When a liquid diluent is employed, it should preferably be a good solvent for the starting materials, inert under the reaction conditions, and of such a nature that separation from the product will not be difficult. For instance, the boiling points of the diluent and the product should differ by an adequate amount and there should be no tendency of the diluent to form an azeotrope with the desired product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred.

Illustrative gaseous diluents include for example, nitrogen, methane, hydrogen, carbon monoxide or carbon dioxide. The gaseous diluent should of course be chosen so that it does not prevent the preparation of the desired products.

While the use of such diluents may be beneficial, the process of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

The alkoxylates of carboxylated compounds produced by the process of this invention can be separated by distillation. For example, a crude reaction product can be subjected to a distillation-separation at atmospheric or reduced pressure through a packed distillation column. Reactive distillation may be useful in conducting the reaction.

The process of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The process of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the catalyst.

The process of this invention is conducted for a period of time sufficient to produce the alkoxylates of carboxylated compounds. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Alkoxylates of carboxylated compounds prepared by the process of this invention comprise alkoxylation species that can be represented by the formulae

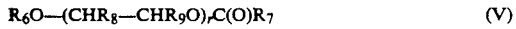  (V)

  (VI)

  (VI)

wherein $R_6$ is the residue of an organic compound, $R_7$ is the residue of an organic compound, $R_8$ and $R_9$ are the same or different and are hydrogen or substituted or unsubstituted alkyl, and r is an integer having a value of at least 1. It is appreciated that for carbonic acid esters, the alkylene oxide or derivatives thereof can exchange with either alkoxide moiety of the carbonic acid ester resulting in a mixture of alkoxylated carbonic acid ester derivatives having the same or different amounts of alkoxylation on the alkoxide moieties.

Illustrative of suitable alkoxylates of carboxylated compounds which can be prepared by the process of this invention include any permissible alkoxylated derivatives of described carboxylated compounds, which are described in Kirk-Othmer, Encyclopedia of Chemical Technology, Third Edition, 1984, the pertinent portions of which are incorporated herein by reference.

Illustrative of suitable reactants in effecting the process of this invention include by way of example:
DMC—dimethyl carbonate
DEC—diethyl carbonate
EO—ethylene oxide
PO—propylene oxide
DBC—dibutyl carbonate
MA—methyl acetate
BA—butyl acetate
DA—dodecyl acetate
FAA—fatty alcohol acetate
NPA—nonyl phenol acetate
DAA—diallyl acetate
DMA—N,N-dimethylamino acetate
DPC—diphenyl carbonate
MPC—methyl 1-piperazine carboxylate
BMC—bis(2-methoxyethyl)carbonate
BMEC—bis[2-(2-methoxyethyl)ethyl]carbonate Illustrative of suitable products prepared by the process of this invention include by way of example:
SEL—(poly)ethylene glycol dimethyl and diethyl ether carbonates
TERF—fatty alcohol alkoxylate carbonates or acetates
TERN—nonyl phenol alkoxylate carbonates or acetates
PEG—poly(oxyalkylene)glycol carbonates or acetates
APEG—alkoxy or allyloxy poly(oxyalkylene)glycol carbonates or acetates
PEPG—poly(oxyethylene)(oxypropylene)glycol carbonates or acetates
UC—alkoxy or allyloxy poly(oxyethylene)(oxypropylene)glycol carbonates or acetates
DMEA—N,N-dimethylaminoethoxy acetate
DBPEG—dibutyl poly(oxyalkylene)glycol carbonates
DAPEG—diallyl poly(oxyalkylene)glycol carbonates Illustrative of permissible reactions encompassed within the scope of this invention include, for example, the following reactant/product combinations:

| REACTANT(S) | PRODUCT(S) |
| --- | --- |
| DMC, EO | SEL |
| DMC, EO | PEG |
| MA, EO | APEG |
| BA, EO, PO | UC |
| DA | TERF |
| FAA | TERF |
| NPA | TERN |
| DMC, EO, PO | PEPG |
| DMA | DMEA |
| DBC, EO | DBPEG |
| DAC, EO | DAPEG |

By this invention, alkoxylate mixtures of carboxylated compounds can be provided which have a narrow, but balanced distribution of alkoxylation species. These alkoxylate mixtures can be relatively free from large amounts of substantially higher alkoxylation moieties, i.e, those having at least three more alkoxyl groups than the average peak alkoxylate specie. Advantageously, these narrow distributions can be obtained where the most prevalent alkoxylation moiety has four or greater alkoxy units, that is, in the regions in which conventional catalysts provide a relatively wide range of alkoxylation species.

The alkoxylate mixtures of carboxylated compounds prepared by the process of this invention are characterized as the reaction products of alkylene oxides and carboxylated compounds. The product mixtures can have at least one alkoxylation moiety which constitutes at least about 18, say, about 20 to 30 or 40, and most often about 20 to 30, weight percent of the composition. The alkoxylate mixtures can also have a relatively symmetrical distribution. Hence, the portion of the product mixture having three or more oxyalkylene unit groups than the peak alkoxylation specie is relatively minor, e.g., often less than about 12, say, less than 10, and often about 1 to 10, weight percent of the mixture. Similarly, the alkoxylation species having fewer oxyalkylene groups by three or more oxyalkylene groups from the average peak alkoxylation specie is usually relatively minor, e.g., less than about 15, say, less than about 10, often about 0.5 to 10, weight percent of the composition. Generally, the one oxyalkylene unit higher and the one oxyalkylene unit lower alkoxylates in respect to the most prevalent alkoxylation specie are present in a weight ratio to the most prevalent alkoxylation specie of about 0.6:1 to 1:1.

Preferred alkoxylate mixtures of this invention can correspond to the formula $$P_m = A'x \, e^{-(m-\bar{m})^2/(2.6+0.4\bar{m})}$$

wherein m is the number of oxyalkylene groups for an alkoxylation specie (m must equal at least one) of the composition, $\bar{m}$ is the weight average oxyalkylene number, $A'$ is the weight percent of the most prevalent alkoxylation specie in the mixture and $P_m$ is, within plus or minus two percentage points, the weight percent of the alkoxylation specie having m oxyalkylene groups in the mixture. This distribution relationship generally applies where m is between the amount of $\bar{m}$ minus 4 to the amount of $\bar{m}$ plus 4.

For purposes herein, the average peak alkoxylation specie is defined as the number of oxyalkylene groups of the most prevalent alkoxylation specie when the next higher and lower homologs are each present in a weight ratio to the most prevalent alkoxylation specie of less than 0.9:1. When one of the adjacent homologs is present in a weight ratio greater than that amount, the average peak alkoxylation specie has an amount of oxyalkylene groups equal to the number average of those of the two species. The weight average oxyalkylene number is the weight average of the oxyalkylene groups of the alkoxylation species in the mixture, i.e., $\bar{m}$ equals the sum of $(m)(P_m)$ for all the species present divided by 100.

Moreover, the relatively symmetrical distribution of alkoxylate species that can be provided by this invention enhances that balance while providing a mixture that exhibits desirable physical properties. For many alkoxylation mixtures of this invention, the species falling within the range of $\bar{m}$ plus or minus two comprise at least about 75, about 80 to 95, sometimes 85 to 95, weight percent of the composition. Importantly, the compositions can be provided such that no single alkoxylation product is in an amount of greater than 50 weight percent of the composition, and, most often, the most prevalent specie is in an amount of 20 to about 30 weight percent, e.g., about 22 to 28, weight percent, to enhance the balance of the composition.

A preferred class of alkoxylate mixtures of carboxylated compounds are the ethylene glycol dialkyl ether carbonates which can undergo decarboxylation to afford (poly)ethylene glycol dialkyl ethers, e.g., SELEXOL® materials, such as monoethylene glycol dimethyl or diethyl ether (glyme and ethyl glyme), diethylene glycol dimethyl or diethyl ether (diglyme and ethyl diglyme), triethylene glycol dimethyl or diethyl ether (triglyme and ethyl triglyme), tetraethylene glycol dimethyl or diethyl ether (tetraglyme and ethyl tetraglyme), polyethylene glycol dimethyl or diethyl ethers (polyglymes and ethyl polyglymes) and the like.

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

I claim:

1. A process for the alkoxylation of a carboxylated compound comprising contacting the carboxylated compound with an alkylene oxide in the presence of a mixed metal oxide catalyst under conditions effective to alkoxylate the carboxylated compound, wherein the mixed metal oxide catalyst comprises:

(a) a material having the formula

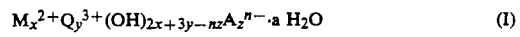  (I)

$$M_x^{2+} Q_y^{3+} (OH)_{2x+3y-nz} A_z^{n-} \cdot a\, H_2O \qquad (I)$$

wherein M is at least one divalent metal cation; Q is at least one trivalent metal cation; and A is at least one anion providing a valence (n−), wherein n is 1 to 4 and wherein a is a positive number, M, Q and A are provided in a proportion such that x/y is a number equal to or greater than 1, z has a value greater than zero and $2x+3y-nz$ is a positive number, or (b) a material prepared by calcining the material of formula (I) having the formula

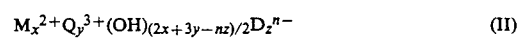  (II)

$$M_x^{2+} Q_y^{3+} (OH)_{(2x+3y-nz)/2} D_z^{n-} \qquad (II)$$

wherein M, Q, x, y, z and n have the same meanings defined above in connection with formula (I), and D is at least one nonvolatile anion.

2. The process of claim 1 wherein the carboxylated compound comprises a substituted or unsubstituted carboxylated compound.

3. The process of claim 1 wherein the carboxylated compound comprises a substituted or unsubstituted ester, carbonic acid ester or carbamic acid ester.

4. The process of claim 1 wherein the carboxylated compound comprises a material having the formulae:

$$ROC(O)R_1 \text{ or } ROC(O)R_2$$

wherein R is the residue of an organic compound, $R_1$ is the residue of an organic compound, and $R_2$ is the residue of an organic compound.

5. The process of claim 1 wherein the carboxylated compound comprises a material having the formulae:

$$ROC(O)OR_1 \text{ or } ROC(O)OR_2$$

wherein R is the residue of an organic compound, $R_1$ is the residue of an organic compound, and $R_2$ is the residue of an organic compound.

6. The process of claim 1 wherein the carboxylated compound comprises a material having the formulae:

$$RN(C(O)OR_1)R \text{ or } RN(C(O)OR_2)R$$

wherein R is the residue of an organic compound, $R_1$ is the residue of an organic compound, and $R_2$ is the residue of an organic compound.

7. The process of claim 1 wherein the carboxylated compound comprises dimethyl carbonate, diethyl carbonate, methyl acetate, dodecyl acetate, N,N-dimethylamino acetate, methyl 1-piperazine carboxylate, ethyl 1-piperazine carboxylate, bis(2-methoxyethyl)carbonate, bis[2-(2-methoxyethoxy)ethyl]carbonate, diphenyl carbonate, diallyl acetate, fatty alcohol acetate or nonyl phenol acetate.

8. The process of claim 1 wherein the alkylene oxide comprises ethylene oxide.

9. The process of claim 1 wherein the alkylene oxide comprises ethylene oxide, propylene oxide or mixtures thereof.

10. The process of claim 1 wherein x/y is a number between 1 and 12 and z has a value which satisfies the relationship: x/z is between n and 12n.

11. The process of claim 1 wherein A is selected from the group consisting of carbonate, halide, phosphite, phosphate, chromate, sulfate, hydroxide, oxalate, acetate, nitrate, hexanoate, sebacate, vanadate, molybdate, tungstate and ferrocyanate.

12. The process of claim 1 wherein D is selected from the group consisting of halides, phosphite, phosphate, vanadate, molybdate, tungstate, sulfite, sulfate, chromate, arsenate, borate and chlorate.

13. The process of claim 1 wherein x/y is a number between 1 and 6 and z has a value which satisfies the relationship: x/z is between n and 6n.

14. The process of claim 1 wherein said material prepared by calcining the material of formula (I) has been heat treated at a temperature in the range of 200° C. to 800° C. for 12 to 24 hours.

15. The process of claim 1 wherein M is magnesium and Q is aluminum.

16. A process of for the alkoxylation of a carboxylated compound comprising contacting the carboxylated compound with an alkylene oxide in the presence of a modified bimetallic or polymetallic catalyst under conditions effective to alkoxylate the carboxylated polymetallic catalyst comprises a material having the formula:

$$[R_4\text{-}X_1\text{-}M_1]_f\text{-}Y_1\text{-}[M_3\text{-}Y_2]_j\text{-}[M_2\text{-}X_2\text{-}R_5]_g$$

wherein:
$R_4$ and $R_5$ are independently hydrogen or the residue of an organic compound having at least one active hydrogen;

$X_1$ and $X_2$ are independently oxygen, sulfur or nitrogen;

$M_1$, $M_2$ and $M_3$ are independently a divalent or polyvalent metal;

$Y_1$ and $Y_2$ are independently a divalent or polyvalent oxyacid anion of valence 2 to 6, oxygen, sulfur or nitrogen provided at least one of $Y_1$ and $Y_2$ is a divalent or polyvalent oxyacid anion of valence 2 to 6;

j is an integer having a value of from 0 to about 100; and f and g are integers having a value such that the sum f+g is equal to the valence of $Y_1$ when j has a value of 0, and f and g are integers having a value such that the sum f+g is equal to the valence of $Y_1$ plus $[M_3\text{-}Y_2]_j$ when j has a value other than 0.

17. The process of claim 16 wherein the divalent or polyvalent oxyacid anion comprises sulfates, phosphates, manganates, titanates, tantalates, molybdates, vanadates, chromates, zirconates and polyphosphates.

18. The process of claim 16 wherein the divalent or polyvalent metal comprises calcium, magnesium, strontium, barium, lanthanum, titanium, zirconium, hafnium, vanadium, niobium, tantalum, chromium, molybdenum, tungsten, manganese, iron, cobalt, nickel, copper, zinc, cadmium, mercury, boron, aluminum, gallium, indium, thallium, carbon, silicon, germanium, tin, lead, phosphorus, arsenic, antimony, sulfur, selenium and tellurium.

19. The process of claim 16 wherein the modified bimetallic or polymetallic catalyst comprises a modified calcium catalyst or a modified magnesium catalyst.

20. The process of claim 1 wherein the product comprises a substituted or unsubstituted alkoxylated carboxylated compound.

21. The process of claim 1 wherein the product comprises a substituted or unsubstituted alkoxylated ester, alkoxylated carbonic acid ester or alkoxylated carbamic acid ester.

22. The process of claim 21 wherein the substituted or unsubstituted alkoxylated ester comprises alkoxylation species represented by the formula $$R_6O\text{—}(CHR_8\text{—}CHR_9O)_r\text{C}(O)R_7$$

wherein $R_6$ is the residue of an organic compound, $R_7$ is the residue of an organic compound, $R_8$ and $R_9$ are the same or different and are hydrogen or substituted or unsubstituted alkyl, and r is an integer having a value of at least 1.

23. The process of claim 21 wherein the substituted or unsubstituted alkoxylated carbonic acid ester comprises alkoxylation species represented by the formula $$R_6O\text{—}(CHR_8\text{—}CHR_9O)_r\text{C}(O)OR_7$$

wherein $R_6$ is the residue of an organic compound, $R_7$ is the residue of an organic compound, $R_8$ and $R_9$ are the same or different and are hydrogen or substituted or unsubstituted alkyl, and r is an integer having a value of at least 1.

24. The process of claim 21 wherein the substituted or unsubstituted alkoxylated carbamic acid ester comprises alkoxylation species represented by the formula $$R_6O-(CHR_8-CHR_9O)_rC(O)NR_7$$

wherein $R_6$ is the residue of an organic compound, $R_7$ is the residue of an organic compound, $R_8$ and $R_9$ are the same or different and are hydrogen or substituted or unsubstituted alkyl, and r is an integer having a value of at least 1.

25. The process of claim 1 wherein the ratio of moles of alkylene oxide to moles of carboxylated compound is from about 0.5:1 to about 1000:1 or greater.

26. The process of claim 1 wherein the product is characterized by a mixture having at least one alkoxylation moiety which constitutes about 18 to 40 weight percent of the mixture; the weight percent of the mixture having three or more oxyalkylene units than the average peak alkoxylation specie is less than about 12 weight percent of the mixture; the alkoxylation specie having one oxyalkylene group more than that of the most prevalent specie and the alkoxylation specie having one oxyalkylene group less than that of the most prevalent specie are present in a weight ratio to the most prevalent specie of about 0.6:1 to 1:1.

27. The process of claim 1 wherein the product is characterized by a mixture which has an alkoxylation specie distribution corresponding to the formula $$P_m = A' \times e^{-(m-\overline{m})2/(2.6+0.4\overline{m})}$$

wherein m is an integer of at least one and is the number of oxyalkylene groups for an alkoxylation specie of the mixture, $\overline{m}$ is the weight average oxyalkylene number of the mixture, $A'$ is the weight percent of the most prevalent alkoxylation specie in the mixture and $P_m$ is, within plus or minus two percentage points, the weight percent of the alkoxylation specie having m oxyalkylene groups in the mixture.

* * * * *

UNITED STATES PATENT AND TRADEMARK OFFICE
CERTIFICATE OF CORRECTION

PATENT NO. : 5,191,104

DATED : March 2, 1993

INVENTOR(S) : Stephen W. King

It is certified that error appears in the above-identified patent and that said Letters Patent is hereby corrected as shown below:

Column 23:
Claim 16, line 5, after "carboxylated" insert --compound, wherein the modified bimetallic or--.

Signed and Sealed this

Seventh Day of June, 1994

Attest:

BRUCE LEHMAN

Attesting Officer     Commissioner of Patents and Trademarks